US00PP16048P2

(12) United States Plant Patent
de Vries

(10) Patent No.: US PP16,048 P2
(45) Date of Patent: Oct. 18, 2005

(54) ***CORYLUS* PLANT NAMED 'RED MAJESTIC'**

(50) Latin Name: *Corylus avellana*
Varietal Denomination: Red Majestic

(75) Inventor: Rolf de Vries, Wiefelstede (DE)

(73) Assignee: Spring Meadow Nursery, Inc., Grand Haven, MI (US)

( * ) Notice: Subject to any disclaimer, the term of this patent is extended or adjusted under 35 U.S.C. 154(b) by 1 day.

(21) Appl. No.: 10/945,154

(22) Filed: Sep. 20, 2004

(51) Int. Cl.[7] ..... A01H 5/00
(52) U.S. Cl. ..... Plt./226
(58) Field of Search ..... Plt./226

(56) References Cited

PUBLICATIONS

UPOV 'hits' on 'Red Majestic', UPOV–Rom, GTI Jpuve Retrieval Software, Plant Variety Databases, 2004/06.*

* cited by examiner

*Primary Examiner*—Anne Marie Grunberg
(74) *Attorney, Agent, or Firm*—C. A. Whealy

(57) ABSTRACT

A new and distinct cultivar of *Corylus* plant named 'Red Majestic', characterized by its compact and outwardly spreading to semi-weeping plant habit; twisting stems; and rich dark burgundy-colored developing leaves and rich dark burgundy-colored fully expanded leaves during the spring and summer.

1 Drawing Sheet

Botanical classification/cultivar designation: *Corylus avellana* cultivar Red Majestic.

BACKGROUND OF THE INVENTION

The present Invention relates to a new and distinct cultivar of *Corylus* plant, botanically known as *Corylus avellana*, and hereinafter referred to by the name 'Red Majestic'.

The new *Corylus* originated from a chance cross-pollination in 1997 of two unidentified selections of *Corylus avellena*, not patented. The cultivar Red Majestic was discovered and selected by the Inventor as a single plant within the progeny of the stated cross-pollination in a controlled environment in Bad Zwischenahn, Germany.

Asexual reproduction of the new cultivar by softwood cuttings at Bad Zwischenahn, Germany since 1997, has shown that the unique features of this new *Corylus* are stable and reproduced true to type in successive generations of asexual reproduction.

SUMMARY OF THE INVENTION

The following traits have been repeatedly observed and are determined to be the unique characteristics of 'Red Majestic'. These characteristics in combination distinguish 'Red Majestic' as a new and distinct cultivar:

1. Compact and outwardly spreading to semi-weeping plant habit.
2. Twisting stems.
3. Rich dark burgundy-colored developing leaves and rich dark burgundy-colored fully expanded leaves during the spring and summer.

In side-by-side comparisons conducted in Grand Haven, Mich., plants of the new *Corylus* differed primarily from plants of the *Corylus avellena* cultivar Contorta, not patented, and other cultivars and selections of *Corylus avellena* known to the Inventor primarily in leaf coloration and plant size as plants of the cultivar Contorta and other cultivars and selections of *Corylus avellena* had greencolored leaves and were larger than plants of the new *Corylus*.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical plant of 'Red Majestic'.

The photograph at the bottom of the sheet is a close-up view of typical leaves of 'Red Majestic'.

Foliage colors in the photographs may differ slightly from the color values cited in the detailed botanical description which accurately describe the colors of the new *Corylus*.

DETAILED BOTANICAL DESCRIPTION

The cultivar Red Majestic has not been observed under all possible environmental conditions. The phenotype may vary somewhat with variations in environment such as temperature and light intensity, without, however, any variance in genotype. The aforementioned photograph and following observations and measurements describe plants grown in Grand Haven, Mich., under commercial practice in an outdoor nursery during the fall and spring. Plants used for the photographs and description were about four years old. In the following description, color references are made to The Royal Horticultural Society Colour Chart, 1995 Edition, except where general terms of ordinary dictionary significance are used.

Botanical classification: *Corylus avellana* cultivar Red Majestic.

Parentage:

*Male, or pollen, parent.*—Unidentified *Corylus avellana* selection, not patented.

*Female, or seed, parent.*—Unidentified *Corylus avellana* selection, not patented.

Propagation:

*Type cutting.*—Softwood cuttings.

*Time to initiate roots.*—About 30 days at 20° C.

*Time to produce a rooted young plant.*—About one year at 25° C.

*Root description.*—Fine to thick; freely branching; creamy white in color.

Plant description:

*General appearance.*—Perennial shrub. Compact and outwardly spreading to semi-weeping plant habit; roughly rounded in shape.

*Growth and branching habit.*—Freely branching; about 15 lateral branches develop per plant. Pinching, that is, removal of the terminal apices, enhances branching with lateral branches potentially forming at every node. Strong and moderately vigorous growth habit. Stems twisting or "zig-zagged".

*Plant height.*—About 1 meter.

*Plant diameter or spread.*—About 1 meter.

*Lateral branch description.*—Length: About 6 cm. Diameter: About 5 mm. Internode length: About 1.3 cm. Texture: Smooth, glabrous. Strength: Strong. Color, immature: 178A. Color, mature: 197A.

*Foliage description.*—Arrangement: Alternate, simple. Length: About 12 cm. Width: About 10 cm. Shape: Oblong to ovate. Apex: Obtuse to acute. Base: Auriculate to cordate. Margin: Serrate. Texture, upper and lower surfaces: Slightly pubescent. Venation pattern: Pinnate. Color: Developing foliage, upper and lower surfaces: 187A. Fully expanded foliage, upper surface: Spring and summer, 183B; late summer and fall, 139A. Fully expanded foliage, lower surface: Spring and summer, 178A; late summer and fall, 137A. Venation, upper surface: Spring and summer, 183B; late summer and fall, 139A. Venation, lower surface: Spring and summer, 178A; late summer and fall, 138B. Petiole: Length: About 1 cm. Diameter: About 2.5 mm. Texture, upper and lower surfaces: Pubescent. Color, upper surface: Spring and summer, 183B; late summer and fall, 139A. Color, lower surface: Spring and summer, 178A; late summer and fall, 138B.

Flower description: Flower development has not been observed on plants of the new *Corylus*.

Disease/pest resistance: Plants of the new *Corylus* have not been observed to be resistant to pathogens and pests common to *Corylus*.

Temperature tolerance: Plants of the new *Corylus* have been observed to tolerate temperatures from −28 to 34° C.

It is claimed:

1. A new and distinct cultivar of *Corylus* plant named 'Red Majestic', as illustrated and described.

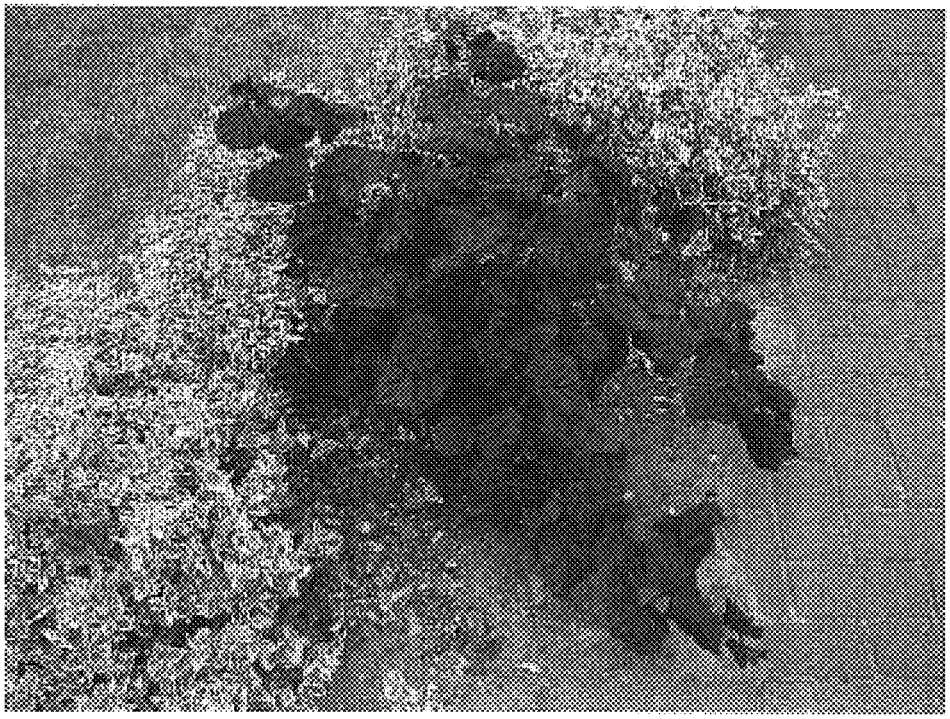
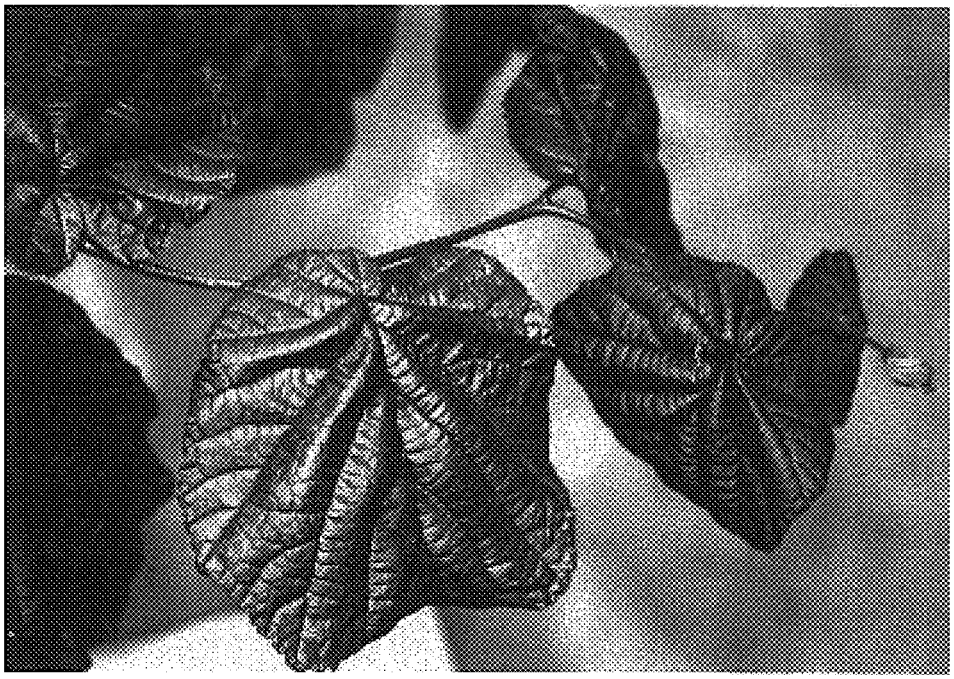

* * * * *